United States Patent [19]

Berthold

[11] Patent Number: 4,510,150

[45] Date of Patent: Apr. 9, 1985

[54] PHARMACEUTICAL COMPOSITIONS EFFECTIVE AGAINST CORONARY HEART DISEASE AND HYPERTENSION

[75] Inventor: Richard Berthold, Bottmingen, Switzerland

[73] Assignee: Sandoz Ltd., Basel, Switzerland

[21] Appl. No.: 519,002

[22] Filed: Aug. 1, 1983

Related U.S. Application Data

[63] Continuation of Ser. No. 302,900, Sep. 16, 1981, abandoned.

[30] Foreign Application Priority Data

Sep. 18, 1980 [GB] United Kingdom ............... 8030226

[51] Int. Cl.³ .............................................. A61K 31/44
[52] U.S. Cl. .................................................... 514/338
[58] Field of Search ......................................... 424/263

[56] References Cited

U.S. PATENT DOCUMENTS

| | | | |
|---|---|---|---|
| 3,832,470 | 8/1974 | Russek | 424/330 |
| 3,911,136 | 10/1975 | Ferrari | 424/330 X |
| 4,046,898 | 9/1977 | Shaw | 548/324 X |
| 4,144,340 | 3/1979 | Offermanns et al. | 544/273 X |

OTHER PUBLICATIONS

*Chemical Abstracts*, 92:94,404j (1980) [Neumann, Eur. Pat. Appl. No. 0,150, 1/10/79].
*Chemical Abstracts*, 93:239,419a (1980) [Neumann, Ger. Offen. No. 2,949,464, 6/26/80].
*Chemical Abstracts*, 93:239,420u (1980) [Neumann, Ger. Offen. No. 2,949,491, 6/26/80].
Hiwatari, M., et al., *Arzneim.-Forsch./Drug. Res.* 29(I), No. 2, 256-260 (1979).
Aoki, K., et al., *Am. Heart J.*, 96(2), 218-226 (1978).
Motté, G., et al., *La Nouvelle Presse Medicale*, vol. 9, No. 6, pp. 379 and 380 (1980).
Wade, A. (Editor), *The Extra Pharmacopoeia*, 27th Ed., The Pharmaceutical Press, London, 1977, p. 1663.
Kaufmann, R., et al., Advances in β-Blocker Therapy (Proc. from the 1st Inter. Bayer β-Blocker Symp. held in May, 1980) *Exc. Med., pp. 111-119.*

*Primary Examiner*—Richard A. Schwartz
*Attorney, Agent, or Firm*—Gerald D. Sharkin; Robert S. Honor; Joseph J. Borovian

[57] ABSTRACT

Pharmaceutical composition containing as active agents (A) a calcium antagonist of a 4-(2,1,3-benz-oxa- or thiadiazoly)-1,4-dihydro pyridine type and (B) a β-blocker and/or a vasodilating nitrate, effective against coronary heart disease and hypertension.

18 Claims, No Drawings

PHARMACEUTICAL COMPOSITIONS EFFECTIVE AGAINST CORONARY HEART DISEASE AND HYPERTENSION

This is a continuation of application Ser. No. 302,900, filed Sept. 16, 1981, now abandoned.

The invention relates to new pharmaceutical compositions effective against coronary heart disease and hypertension, and to their production and use. The present invention provides a pharmaceutical composition containing as active agents (A) a compound of formula I,

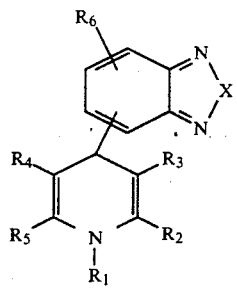

wherein $R_1$ is hydrogen, $(C_{1-6})$alkyl, hydroxy$(C_{2-6})$alkyl, $(C_{3-6})$alkoxyalkyl, $(C_{3-6})$alkenyl, $(C_{3-6})$alkinyl, $(C_{3-7})$cycloalkyl, $(C_{4-8})$cycloalkylalkyl, $(C_{7-9})$phenylalkyl or $(C_{9-12})$phenylalkenyl, the phenyl ring being unsubstituted or independently mono-, di- or trisubstituted by halogen, hydroxy, $(C_{1-4})$alkyl or $(C_{1-4})$alkoxy, $R_2$ and $R_5$, independently, are hydrogen, $(C_{1-6})$alkyl, $(C_{7-10})$phenylalkyl, $(C_{3-7})$cycloalkyl or $(C_{4-8})$cycloalkylalkyl, $R_3$ and $R_4$, independently are CN, $COOR_7$, $COR_8$, $S(O)_nR_9$, or

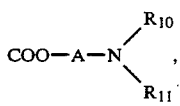

wherein n is 0, 1 or 2, $R_7$, $R_8$ and $R_9$ independently are $(C_{1-6})$alkyl, $(C_{3-6})$alkenyl, $(C_{3-6})$alkinyl, $(C_{3-7})$cycloalkyl, $(C_{4-8})$cycloalkylalkyl, hydroxy$(C_{2-6})$alkyl, $(C_{3-6})$alkoxyalkyl, hydroxy$(C_{4-8})$alkoxyalkyl, amino$(C_{2-6})$alkyl, $(C_{1-4})$alkylamino$(C_{2-6})$alkyl, di[$(C_{1-4})$alkyl]aminoalkyl, phenyl, $(C_{7-10})$phenylalkyl, a 5- or 6-membered heterocyclic ring containing one heteroatom selected from nitrogen, oxygen or sulphur and which may contain additionally 1, 2 or 3 ring nitrogen atoms, or $(C_{1-4})$alkyl substituted by a 5- or 6-membered heterocyclic ring containing one heteroatom selected from nitrogen, oxygen or sulphur and which may contain additionally 1, 2 or 3 ring nitrogen atoms, A is $(C_{1-6})$alkylene, $R_{10}$ and $R_{11}$ independently are $(C_{1-6})$alkyl, $(C_{3-6})$alkenyl or $(C_{3-6})$alkinyl, $(C_{3-7})$cycloalkyl, $(C_{4-8})$cycloalkylalkyl, hydroxy$(C_{2-6})$alkyl, $(C_{3-6})$alkoxyalkyl, hydroxy$(C_{4-8})$alkoxyalkyl, amino$(C_{2-6})$alkyl, $(C_{1-4})$alkylamino$(C_{2-6})$alkyl, di[$C_{1-4}$)alkyl]aminoalkyl, phenyl, $(C_{7-10})$phenylalkyl, or $R_{10}$ and $R_{11}$ together with the nitrogen atom form a 5-, 6- or 7-membered heterocyclic ring, which may contain a further heteromember selected from oxygen, sulphur and a group $=N-R_{12}$, wherein $R_{12}$ is $(C_{1-4})$alkyl, and $R_6$ is hydrogen, halogen, $(C_{1-4})$alkyl, $(C_{1-4})$alkoxy, $(C_{1-4})$alkylthio, $(C_{1-4})$alkylsulfonyl, trifluoromethyl, nitro, hydroxy, azido, amino, $(C_{1-4})$alkylamino, di[$(C_{1-4})$alkyl]amino, $(C_{1-5})$alkanoylamino, $(C_{2-5})$carbalkoxy, aminocarbonyl, trifluoromethoxy, cyano, sulfamyl, $(C_{1-4})$alkylsulfamyl or di[$(C_{1-4})$alkyl]sulfamyl, and X is oxygen or sulphur, in free base or in a pharmaceutically acceptable acid addition salt form and (B) a β-adrenoceptor blocking agent and/or (C) a vasodilating nitrate, hereinafter referred to as a composition of the invention.

The components (A), (B) and (C) of the composition are generally known. Particularly the compounds of formula I are known from e.g. European Patent Publication No. EP 150 (application No. 78100165.6), U.K. Patent Publication No. 20 41 358 (application No. 7943112) and U.K. Patent Publication No. 20 37 766 (application No. 7943113).

In any of the above radicals for active component (A) of formula I, alkyl of 1 to 6 carbon atoms is preferably of 1 to 4 carbon atoms, especially of 1 to 2 carbon atoms. Any alkyl, alkoxy, alkylthio or alkylsulfonyl radical of 1 to 4 carbon atoms is preferably of 1 to 2 carbon atoms. The hydroxy, alkoxy, hydroxyalkoxy, amino or alkylamino group of the hydroxyalkyl, alkoxyalkyl, hydroxyalkoxyalkyl, aminoalkyl or alkylaminoalkyl moiety in $COOR_7$ is preferably not attached to the α-carbon atom and is preferably attached to the distant terminal carbon atom. Any hydroxyalkyl, alkoxyalkyl, hydroxyalkoxyalkyl, aminoalkyl or alkylaminoalkyl radical preferably has an ethylene or propylene moiety substituted by hydroxy, alkoxy, hydroxyalkoxy, amino or alkylamino respectively. The alkyl moiety of cycloalkylalkyl is conveniently methyl. Halogen means fluorine, chlorine or bromine and is especially chlorine. Cycloalkyl or the cycloalkyl moiety of cycloalkylalkyl is conveniently cyclopropyl or cyclopentyl or cyclohexyl. The multiple bond of alkenyl, alkinyl or phenylalkenyl in $R_1$ or $COOR_7$ is preferably not in the α,β position. Alkenyl or alkinyl preferably has 3 to 5 carbon atoms. Alkenyl is conveniently allyl or 2-methylallyl. Alkinyl is conveniently propinyl. Phenylalkenyl preferably has the trans-configuration and is for example cinnamyl. When $R_1$ is optionally substituted phenylalkyl, the phenyl group is preferably unsubstituted. When the phenyl group is di- or tri-substituted, preferably the substituents are the same. When $R_7$, $R_8$ or $R_9$ contain a heterocyclic ring this may be for example furyl, thienyl, pyrrolyl, thiazolyl, isothiazolyl, thiadiazolyl, oxazolyl, isoxazolyl, oxadiazolyl, imidazolyl, pyrazolyl, triazolyl, tetrazolyl, pyridyl, pyrimidinyl, pyrazinyl, pyridazinyl, piperidinyl, morpholinyl or triazinyl.

When $R_{10}$ and $R_{11}$ together with the nitrogen atom to which they are bound, form a heterocyclic ring, this is preferably saturated and may be for example pyrrolidine, piperidine, piperazine, N-alkylpiperazine, morpholine, azepane, diazepane or N-alkyl-diazepane.

$R_2$ is conveniently identical to $R_5$.

$R_6$ is conveniently halogen, alkyl or alkoxy, or hydrogen and is conveniently adjacent to the dihydropyridine moiety.

As components (A) the following compounds of formula I, wherein y indicates the position of the dihydropyridine moiety, may be used.

| Compound No. | R₁ | R₂ | R₃ | R₄ | R₅ | R₆ | X | y |
|---|---|---|---|---|---|---|---|---|
| 1 | H | CH₃ | CN | COO—i-Bu | CH₃ | H | O | 4 |
| 2 | H | CH₃ | COOC₂H₅ | SO₂CH₃ | CH₃ | H | O | 4 |
| 3 | H | CH₃ | CN | COOC₂H₅ | CH₃ | H | O | 4 |
| 4 | H | CH₃ | CN | COOC₂H₅ | CH₃ | H | S | 4 |
| 5 | H | CH₃ | CN | COOCH₂CH(CH₃)₂ | CH₃ | H | S | 4 |
| 6 | H | CH₃ | COOCH₃ | COC₆H₅ | CH₃ | H | O | 4 |
| 7 | H | CH₃ | COO(CH₂)₂N(CH₃)(CH₂C₆H₅) | COOC₂H₅ | CH₃ | H | O | 4 |
| 8 | H | CH₃ | COO(CH₂)₂N(CH₃)(CH₂C₆H₅) | COOC₂H₅ | CH₃ | H | S | 4 |
| 9 | H | CH₃ | COO(CH₂)₂N(CH₃)₂ | COO(CH₂)₂N(CH₃)₂ | CH₃ | H | O | 4 |
| 10 | H | CH₃ | COO(CH₂)₂N(CH₃)₂ | COO(CH₂)₂N(CH₃)₂ | CH₃ | H | S | 4 |
| 11 | H | CH₃ | COO(CH₂)₂N(CH₃)₂ | COOC₂H₅ | CH₃ | H | O | 4 |
| 12 | H | CH₃ | COO(CH₂)₂N(CH₃)₂ | COOC₂H₅ | CH₃ | H | S | 4 |
| 13 | H | CH₃ | COO(CH₂)₂N(CH₃)(CH₂C₆H₅) | COOC₂H₅ | CH₃ | H | S | 5 |
| 14 | H | CH₃ | COO(CH₂)₂N(CH₃)(CH₂C₆H₅) | COOC₂H₅ | CH₃ | H | O | 5 |
| 15 | H | CH₃ | COO(CH₂)₂N(CH₃)(CH₂C₆H₅) | COOCH₃ | CH₃ | H | O | 4 |
| 16 | H | Δ | COOC₂H₅ | COOC₂H₅ | CH₃ | H | O | 4 |
| 17 | H | Δ | COOCH₃ | COOCH₃ | CH₃ | H | O | 4 |
| 18 | H | Δ | COOCH₃ | COOCH₃ | Δ | H | O | 4 |
| 19 | H | Δ | COOC₂H₅ | COOC₂H₅ | Δ | H | O | 4 |
| 20 | H | CH₃ | COO(CH₂)₂—C₆H₅ | COOCH₃ | CH₃ | H | O | 4 |
| 21 | H | CH₃ | COOCH₃ | COOCH₂C₆H₅ | CH₃ | H | O | 4 |
| 22 | H | CH₃ | COOC₂H₅ | COOC₂H₅ | CH₃ | H | O | 4 |
| 23 | H | CH₃ | COOC₂H₅ | COOC₂H₅ | CH₃ | H | S | 4 |
| 24 | H | CH₃ | COOC(CH₃)₃ | COOC(CH₃)₃ | CH₃ | H | S | 4 |
| 25 | H | CH₃ | COOCH₃ | COOCH₃ | CH₃ | 7-Cl | O | 4 |
| 26 | H | CH₃ | COOCH₃ | COOCH₃ | CH₃ | H | S | 4 |
| 27 | H | CH₃ | COOC₂H₅ | COOC₂H₅ | CH₃ | 5-OCH₃ | S | 4 |
| 28 | H | CH₃ | COOC₂H₅ | COOC₂H₅ | CH₃ | 7-Cl | S | 4 |
| 29 | H | CH₃ | COOC₂H₅ | COOC₂H₅ | CH₃ | H | S | 5 |
| 30 | H | CH₃ | COOC₂H₅ | COOC₂H₅ | CH₃ | 4-Cl | S | 5 |
| 31 | H | CH₃ | COC(CH₃)₃ | COC(CH₃)₃ | CH₃ | H | S | 4 |
| 32 | H | CH₃ | COCH₃ | COCH₃ | CH₃ | 7-Cl | O | 4 |
| 33 | H | CH₃ | COCH₃ | COCH₃ | CH₃ | H | S | 4 |
| 34 | H | CH₃ | COC₂H₅ | COC₂H₅ | CH₃ | 5-OCH₃ | S | 4 |
| 35 | H | CH₃ | COC₂H₅ | COC₂H₅ | CH₃ | 7-Cl | S | 4 |
| 36 | H | CH₃ | COC₂H₅ | COC₂H₅ | CH₃ | H | S | 5 |
| 37 | H | CH₃ | COC₂H₅ | COC₂H₅ | CH₃ | 4-Cl | S | 5 |
| 38 | H | CH₃ | COCH₃ | COCH₃ | CH₃ | H | O | 4 |
| 39 | H | CH₃ | COCH₃ | COOC₂H₅ | CH₃ | H | O | 4 |
| 40 | H | CH₃ | COCH₃ | COOC₂H₅ | CH₃ | H | S | 4 |
| 41 | H | CH₃ | COOCH₂CH(CH₃)₂ | COOCH₃ | CH₃ | H | O | 4 |
| 42 | H | CH₃ | COOCH₃ | COOCH₃ | CH₃ | H | O | 4 |
| 43 | H | CH₃ | COOC₂H₅ | COOC₂H₅ | CH₃ | H | O | 5 |
| 44 | H | CH₃ | COOCH₂CH(CH₃)₂ | COOC₂H₅ | CH₃ | H | S | 4 |
| 45 | H | CH₃ | COOCH₂CH(CH₃)₂ | COOC₂H₅ | CH₃ | H | O | 4 |
| 46 | H | CH₃ | COOC(CH₃)₃ | COOC(CH₃)₃ | CH₃ | H | O | 4 |
| 47 | H | CH₃ | COOCH₂CH(CH₃)₂ | COOCH₂CH(CH₃)₂ | CH₃ | H | O | 4 |
| 48 | H | CH₃ | COO(CH₂)₂OC₂H₅ | COOC₂H₅ | CH₃ | H | O | 4 |
| 49 | H | CH₃ | COO(CH₂)₂OC₂H₅ | COOC₂H₅ | CH₃ | H | S | 4 |
| 50 | H | CH₃ | COO(CH₂)₂OC₂H₅ | COOC₂H₅ | CH₃ | H | S | 5 |
| 51 | H | CH₃ | COOCH(CH₃)₂ | COOCH₃ | CH₃ | H | O | 4 |
| 52 | H | CH₃ | COO(CH₂)₂OCH₃ | COOCH₃ | CH₃ | H | O | 4 |

-continued

As components (A) the following compounds of formula I, wherein y indicates the position of the dihydropyridine moiety, may be used.

| Compound No. | $R_1$ | $R_2$ | $R_3$ | $R_4$ | $R_5$ | $R_6$ | X | y |
|---|---|---|---|---|---|---|---|---|
| 53 | H | $CH_3$ | $COO(CH_2)_2OCH(CH_3)_2$ | $COOCH_3$ | $CH_3$ | H | O | 4 |
| 54 | H | $CH_3$ | $COO(CH_2)_2OC_2H_5$ | $COOCH_3$ | $CH_3$ | H | O | 4 |
| 55 | H | $CH_3$ | 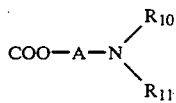 | $COOCH_3$ | $CH_3$ | H | O | 4 |
| 56 | H | $CH_3$ | $COO(CH_2)_2OCH_3$ | $COOCH(CH_3)_2$ | $CH_3$ | H | O | 4 |
| 57 | H | $CH_3$ | $COOCH_3$ | $COOC_2H_5$ | $CH_3$ | H | O | 4 |
| 58 | $CH_3$ | $CH_3$ | $COOC_2H_5$ | $COOC_2H_5$ | $CH_3$ | H | O | 4 |
| 59 | $n-C_3H_7$ | $CH_3$ | $COOC_2H_5$ | $COOC_2H_5$ | $CH_3$ | H | O | 4 |

Preferred compositions of the invention contain a component (A) of formula I in which $R_1$ is hydrogen or $(C_{1-6})$alkyl or $R_2$ and $R_5$ independently are $(C_{1-6})$alkyl or the dihydropyridine ring is in position 4 of the benzoxa- or -thia diazolyl moiety or X is oxygen or $R_6$ is hydrogen or $R_3$ and $R_4$ independently are $COOR_7$, $COR_8$ or

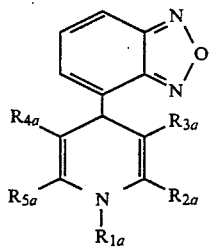

in which $R_7$, $R_8$, $R_{10}$, $R_{11}$ and A are as defined above. However, $R_7$ is preferably $(C_{1-6})$alkyl, $(C_{3-6})$alkoxyalkyl, $(C_{3-7})$cycloalkyl or $(C_{7-10})$phenylalkyl, $R_8$ is preferably $(C_{1-6})$alkyl and preferably one of $R_{10}$ and $R_{11}$ is $(C_{1-6})$alkyl and the other $(C_{7-10})$phenylalkyl and A is preferably $(C_{1-2})$alkylene.

Particularly preferred components (A) are such of formula Ia,

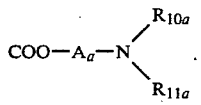  Ia wherein
$R_{1a}$ is hydrogen or $(C_{1-6})$alkyl,
$R_{2a}$ and $R_{5a}$ independently are $(C_{1-6})$alkyl
$R_{3a}$ and $R_{4a}$ independently are $COOR_{7a}$, $COR_{8a}$ or

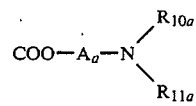

in which
$R_{7a}$ is $(C_{1-6})$alkyl, $(C_{3-6})$alkoxyalkyl, $(C_{3-7})$cycloalkyl or $(C_{7-10})$phenylalkyl,
$R_{8a}$ is $(C_{1-6})$alkyl, one of $R_{10a}$ and $R_{11a}$ is $(C_{1-6})$alkyl, the other is $(C_{7-10})$phenylalkyl and $A_a$ is $(C_{1-2})$alkylene.

In the components (A) of formula Ia, preferably one of $R_{3a}$ and $R_{4a}$ is $COOR_{7a}$ and the other is $COR_{8a}$, or $COOR_{7a}$, in which $R_{7a}$, $R_{8a}$, $A_a$, $R_{10a}$ and $R_{11a}$ are as defined above.

If both $R_{3a}$ and $R_{4a}$ independently are $COOR_{7a}$, preferably one of $R_{3a}$ and $R_{4a}$ is $(C_{2-7})$alkoxycarbonyl and the other is $(C_{4-7})$alkoxyalkoxycarbonyl, $(C_{4-8})$cycloalkoxycarbonyl, $(C_{8-11})$phenylalkoxycarbonyl or $(C_{2-7})$alkoxycarbonyl. If one of $R_{3a}$ and $R_{4a}$ is $(C_{2-7})$alkoxycarbonyl, and the other is $(C_{5-7})$alkoxyalkoxycarbonyl or $(C_{4-7})$alkoxycarbonyl, preferably at most one of the terminal alkoxy groups having at least 4 carbon atoms is branched. Preferred as active components (A) are the compounds having the compound Nos. 7, 21, 22, 39, 41, 45, 48, 51–57 and 59. Especially preferred are the compound Nos. 21, 22, 51, 54 and 55, particularly 22.

A suitable β-adrenoceptor blocking agent (B) is e.g. a compound having an

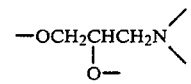

side chain attached through the 1-oxygen thereof directly to an aryl moiety, or a

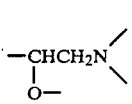

side chain attached through the 1-carbon atom thereof directly to an aryl moiety.

The aryl moiety may be, for example, of up to 10 carbon atoms, e.g. phenyl or naphthyl, e.g. 4-indolyl or 1-naphthyl, and may contain one or two heteroatoms, e.g. nitrogen as in indolyl or nitrogen and sulphur as in thiazolyl. The aryl moiety may also have one or two ring substituents, e.g. acetyl, allyl, allyloxy, aminocarbonylmethyl, cyano, methyl, chloro, methoxy, methoxyethyl, amido, hydroxy, nitro, propinyloxy, $(C_{1-4})$alkanoylamino, methylsulfamoyl, morpholino, methylthio, oxo and tetrahydrofurylmethyloxy substituents.

The aryl moiety may also have an alkyl chain between two adjacent carbon atoms, thereby forming a saturated ring. For example, the aryl moiety nucleus may be tetralone or tetraline.

The amino group of the

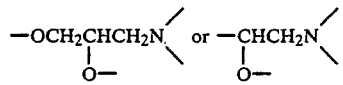

side chain conveniently has a branched chain alkyl substituent of 3 to 7 carbon atoms, e.g. isopropyl or tert-butyl.

Examples of suitable known β-blocking agents are Acebutolol, Alprenolol, Atenolol, Bufetolol, Bunitrolol, Bunolol, Bupranolol, Labetalol, Metoprolol, Nadoxolol, Oxprenolol, Pargolol, Procinolol, Propranolol, Talinolol, Timolol, Tiprenolol, Tolamolol, Toliprolol, Trimepranol.

Preferred as active agents (B) are compounds interfering little with myocardial contractile function and having little effect on heart rate, e.g. compounds possessing some degree of intrinsic sympathomimetic activity.

Especially interesting compounds are:
4-(2-hydroxy-3-isopropylaminopropoxy)indole (Pindolol) and
4-(2-benzoyloxy-3-tert-butylaminopropoxy)-2-methylindole (LT).

Preferred as active components (C) are known ($C_{1-6}$)aliphatic alcohol esters of nitric acid. Especially preferred are ($C_{3-6}$)aliphatic polyol esters of nitric acid, such as glyceryl trinitrate and mannitol hexanitrate, particularly erythrityl tetranitrate and pentaerythritol tetranitrate, especially isosorbide dinitrate.

Active agents (A) and (B) may be in the free base form or in salt, e.g. in acid addition salt form. The new composition may be prepared by a process comprising formulating component (A), with component (B) and/or component (C), in a state of purity sufficient for pharmaceutical acceptability. Conventional pharmaceutical excipients including carriers and diluents, may also be formulated therewith.

Preferred is a composition containing components (A) and (B).

The composition of the invention possesses pharmacological activity in animals and are therefore useful as pharmaceuticals, e.g. for therapy. In particular, the composition of the invention is useful as a calcium-antagonist, as indicated in standard tests, e.g. as follows:

An inhibition of the calcium-induced contraction of isolated dog coronary arteries suspended in a depolarizing solution is observed at a concentration of about $10^{-10}$M to about $10^{-8}$M of active agent (A) (method of Godfraind and Kaba, Brit. J. Pharm. 36 [1969] 549–560).

The composition containing components (A) and (B) is additionally useful as a β-adrenoceptor blocking agent as indicated in the following standard test.

In the isolated, spontaneously-beating guinea pig atrium (method of K. Saameli, Helv. Physiol. Acta [1967] CR 219–CR 221) inhibition of the positive inotropic effect of adrenaline is observed at a bath concentration of about $10^{-9}$ to about $10^{-6}$M of active agent (B). The composition containing components (A) and (C) in addition to its calcium-antagonistic effect is useful as an arterial and venous smooth muscle relaxing agent as indicated in the hemodynamic standard test with the open chest cat in the form of a reduction of preload and afterload.

The composition containing component (A) and component (B) and/or component (C) exhibits antihypertensive activity, as indicated by a blood pressure lowering activity in standard tests.

For example, the composition exhibits a blood pressure lowering effect in the Grollman rat test [see A. Grollman, Proc. Soc. Expt. Biol. and Med. 57, 104 (1944)] as well as in tests carried out in a similar way in spontaneously hypertensive rats on s.c. administration of from 0.1 to 10 mg/kg animal body weight of the composition.

The composition of the invention is therefore useful in the treatment of coronary heart disease, e.g. Angina pectoris, and hypertension.

For the above-mentioned uses the dosage will, of course, vary depending on the compounds employed, the mode of administration and the therapy desired. However, in general, satisfactory results are obtained when active agent (A), e.g. compound No. 22, is administered at a daily dosage of from about 0.01 mg to about 10 mg, particularly of about 0.1 to about 10 mg per kg animal body weight, conveniently given in divided doses 2 to 4 times a day, or in sustained release form. For the larger mammal, the total daily dosage is in the range of from about 5 mg to about 200 mg, particularly from about 5 to about 100 mg, and dosage forms suitable for oral administration comprise from about 1.25 mg to about 100 mg, particularly from about 1.25 to about 50 mg of the compounds admixed with a solid or liquid pharmaceutical carrier or diluent. An indicated preferred weight ratio of active agent (A) to active agent (B), calculated on the free base moiety thereof, is from about 100:1 to about 1:10, particularly from about 100:1 to about 1:1, preferably from about 50:1 to about 5:1. Thus for compound No. 22 and LT a preferred range is from about 100:1 to about 1:1, especially about 50:1. For compound No. 22 and Pindolol a preferred range is from about 10:1 to about 1:10, particularly from about 10:1 to 1:1, especially about 7:1.

An indicated preferred weight ratio of component (A) to component (C), calculated on the free base of component (A), is from about 1:3 to about 10:1, particularly about 10:3. For compound No. 22 and isosorbide dinitrate the preferred range is from about 1:3 to about 10:3, particularly from about 1:3 to about 10:1, especially about 10:3. An indicated preferred weight ratio of component (A) to component (B) to component (C), calculated on the free bases of components (A) and (B), is from about 2:20 to about 0.2:24 to about 2:10.

For compound No. 22, Pindolol and isosorbide dinitrate, the preferred weight ratio is from about 2:20 to about 1:1.5 to about 2:6, particularly about 7:1.5:6.

For compound No. 22, LT and isosorbide dinitrate, the preferred weight ratio is about 70:2:60.

Conveniently components (A) and (B) and/or (C) are administered in the form of a pharmaceutical composition comprising a compound of formula I in free base form or in pharmaceutically acceptable acid addition salt form, and a β-adrenoceptor blocking agent in free base form or in pharmaceutically acceptable salt, e.g. acid addition salt form, and/or ($C_{1-6}$)aliphatic alcohol ester of nitric acid, in association with a pharmaceutical carrier or diluent. Such compositions may be formulated in conventional manner so as to be, for example, a solution, such as an injectable solution, or a tablet.

It has now been found that the composition of the invention surprisingly does not lead to the unfavourable effects that can be expected on the basis of the components (A), (B) and (C) when taken alone. For compositions containing components (A) and (B), surprisingly no clinical observations can be made which indicate that the combination of a β-adrenergic blocking agent and a calcium-antagonist generally may be highly dangerous.

It is known that β-adrenergic blocking agents as well as standard calcium antagonists such as Verapamil and Nifedipine have some degree of cardiodepressant effect. It was therefore to be expected that their use in combination would be dangerous since an interaction in any heart that does not have much functional reserve might precipitate congestive heart failure. This condition of insufficient functional reserve is difficult to exclude completely and is common in patients with severe coronary heart disease.

It has therefore generally been stated that patients should not be simultaneously treated with a calcium antagonist and an adrenergic β-blocking agent. For the combination of Nifedipine and an adrenergic β-blocking agent very conflicting opinions have been expressed. Thus cardiovascular accidents have been reported in cases of concomittant administration of Verapamil and a β-blocking agent (Witchitz, S. et al., *Nouv. Presse Med.* 4 [1975] 337) and of Nifedipine and Atenolol (G. Motté et al., *Nouv. Presse Med.* 9 [1980] 379). Great caution in such simultaneous administration has generally been recommended (K. E. Wirth, *Med. Welt* 29 [1978] 413).

However, to our surprise it has now been found that the dosage of active agent (A) necessary to produce a significant cardiodepressant effect is several orders of magnitude higher than the dosage effective in producing a potent calcium antagonistic effect.

This observation was arrived at as follows:

First the potency of calcium antagonism was determined on coronary arteries in vitro:

Mongrel dogs of either sex weighing between 15 and 30 kg were anaesthetized by rapid i.v. injection of pentobarbitone (50 mg/kg) and killed by i.v. injection of 100 ml of air. The heart was removed and placed in a modified Krebs-Henseleit solution (mM): NaCl 118, KCl 4.7, $MgSO_4$ 1.2, $CaCl_2$ 2.5, $KH_2PO_4$ 1.2, $NaHCO_3$ 25, glucose 11, at 37° C., gassed with 95% $O_2$–5% $CO_2$. Branches of the ventral interventricular artery (about 500 to 1000 μm outer diameter) were dissected and cut into helical strips, approximately 1 to 3 mm wide and 10 mm long.

The strips were suspended in 10 ml organ baths containing Krebs-Henseleit solution at 37° C. gassed continuously with 5% $CO_2$ in oxygen. Changes in the tension of the strips were recorded isometrically with electromechanical transducers (Statham model UC 3) and a potentiometric recorder. At the beginning of the experiments the strips were stretched to an initial tension of 500 mg and then allowed to equilibrate for 120 to 180 minutes in the bathing medium. Thereafter the Krebs-Henseleit solution was replaced by a solution containing 100 mM KCl in equimolar replacement for NaCl. Cumulative response curves for $CaCl_2$ were established, using the method described by Van Rossum, J. M., *Arch. Intern. Pharmacodyn.* 143 (1963) 299. The duration of exposure to a particular concentration depended on the time to reach equilibrium (the maximum response reached with that particular concentration). Thus there was no fixed interval at which the concentration of the agonist were increased. Component (A) or Verapamil was added 30 min. before the first administration of $CaCl_2$. The effects were expressed as percentage of the preceding response to nM $CaCl_2$. In all experiments at least one strip was used as control.

The $pA_2$ values obtained were 10.5 for compound No. 22 and 7.8 for Verapamil.

Then the effects on contractility of paced guinea pig left arteria in vitro was measured:

Guinea pigs of either sex weighing 250 to 400 g were killed by a blow on their heads and the left atrium was rapidly dissected from the heart and suspended in a modified oxygenated Tyrode solution at 30° C. The preload was adjusted to 1 g, rectangular impulses of 10 msec. at a rate of 1 Hz were used for pacing through a platinum cathode attached to the lower end of the tissue. The tension developed was measured isometrically with a Statham UC 3 transducer.

Compound No. 22 or Verapamil was added to the bath in increasing amounts.

The highest dose of compound No. 22, 0.444 μM, reduced the contractile force to 56% of its baseline value. With Verapamil a comparable reduction was obtained at about 1.4 μM. These results should be compared with the results obtained on coronary arteries. In the case of compound No. 22 there is an about 10,000 fold difference between the concentration mentioned and the $pA_2$ of Ca-antagonism whereas for Verapamil this difference is only about 100 fold. This shows that compound No. 22 is about 100 times less cardiodepressant than Verapamil for a similar degree of calcium antagonism. Due to this, selectively component (A) can be combined with agents that have negative influences on myocardial contractility, e.g. beta-blockers. Secondly, it has been found that a combination of active agent (A) with an active agent (B) has unexpected non-additive properties for these undesirable side-effects.

This observation was arrived at in the anaesthetized open chest cat as follows:

The microsphere method as described in 1967 by Rudolph, A. M. and Heymann, M. S. in *Circ. Res.* 21 (1967) 163 and modified by R. P. Hof, F. Wyler and G. Stalder, *Basic Res. Cardial.* 75, 747–756 (1980) was used. Cardiac output was calculated from the flow signal of an electromagnetic flow meter. Since the calibration factors indicated by the producer of the flow probes did not apply to cat aortic blood flow, these probes were calibrated at the end of each experiment with a microsphere injection, using the reference flow method of Buckberg, G. D. et al., *J. of Applied Physiology* 31 (1971), 598–604. This consists in sampling blood at a known flow rate into a syringe, which can be regarded as "an external organ".

This sampling is done during the time of microsphere circulation. The number of microspheres in the syringe is then determined and cardiac output can be calculated as follows:

$$CO = Q_s \times (N_i/N_s)$$

where CO is cardiac output, $Q_s$ is flow to the syringe, $N_i$ is the number of spheres injected and $N_s$ is the number of spheres in the syringe.

Cats of 2 to 4 kg of body weight were anaesthetized with chloralose urethane (43 and 430 mg/kg) and ventilated with a Loosco M.K.II infant ventilator with positive end-expiratory pressure. Catheters were inserted into the femoral artery and vein. The thorax was opened through the left fourth intercostal space, the aorta was freed of its adventitia and an electromagnetic flow probe was placed around it. The electromagnetic flow signal and its first derivative, acceleration of the blood in the aorta, mean aortic flow, phasic and mean aortic blood pressure, heart rate and mean right atrial pressure were recorded on a Beckmann R612 8 channel recorder. For flow measurements a Narco RT500 flowmeter was used. Differentiation was performed by a HSE 401 differentiator. The flow signal, which is a measurement of the velocity of blood in the aortic root was electronically integrated to obtain mean aortic flow. At the same time this signal was fed into the differentiator mentioned. The output of the differentiator, acceleration of blood in the aorta, is an indicator of myocardial function and was used instead of dp/dt (R. R. Rushmer, *Circulation* 29 [1964] 268, G. C. Van den Bos et al., *Cardiovascular Research* 7 [1973] 834), applied to cats by R. P. Hof and A. Hof, *Journal of Pharmacological Methods*, accepted for publication in 1981. At the end of the experiments the cats were dissected and the organs or samples of tissue placed in counting vials. The samples were counted in a Packard Mod. 9012 gamma counter with a 1024 channel pulse height analyser. Component (A), e.g. compound No. 22 was dissolved in polyethyleneglycol 400 1 ml plus ethanol 1 ml per milligram of active substance and administered intravenously at a dose of 43 µg/kg i.v. Coronary blood flow was markedly increased. The experiment was then repeated, with LT being infused intravenously at the dose of 50 µg/kg. After a stabilisation time of 60 minutes, compound No. 22 was then administered exactly as described above to obtain results strikingly similar to those without pretreatment. Thus, the magnitude of change and time course of all relevant general hemodynamic parameters indicative of myocardial contractility, such as acceleration of blood and cardiac output, were comparable in cats not pretreated and in cats pretreated with the β-adrenoceptor blocking agent, which means that the combination of components (A) and (B) is a non-additive one, since β-blockers are known to diminish coronary blood flow. The same was observed with regard to heart rate. The adequacy of betablockage was checked by comparing the effects of a test dose of isoproterenol 0.05 µg/kg before, to the effects of 0.1 µg/kg after the betablockade. All isoproterenol effects were completely or almost completely suppressed by the dose of LT used.

Additionally there can be established that a diminuation of the coronary blood flow, caused by a component (B), is compensated by a component (A) and an increase of the preload caused by component (A) is compensated by component (C). The simultaneous administration of an active agent (A) and an active agent (B) and/or (C) is therefore unexpectedly safe.

The combination of the invention can be used, surprisingly, without untoward cardiodepressant effect, e.g. in cases of hypertension and especially in cases of coronary disease that do not respond satisfactorily when either active agent (A) or active agent (B) or active agent (C) is administered alone.

It is to be appreciated that the beneficial effects of the combination may also be obtained when active agents (A) and (B) and/or (C) are administered separately, in analogous manner to that indicated above, e.g. in the form of pharmaceutical compositions. Thus a therapeutically effective amount of active agent (A) and of active agent (B) and/or (C) may be administered to a subject in need of such treatment.

If desired the active agents may be ordered in a pack to facilitate administration of a particular dosage regimen, e.g. in a particular order in a blister pack. A suitable composition may consist of a pack containing separately active agents (A) and (B) and/or (C) until required for concomitant administration, conveniently together with instructions for the concomitant administration of a predetermined amount of active agent (A) and a predetermined amount of active agent (B) and/or (C).

The following compositions may be formulated using standard encapsulating or tabletting techniques and are useful for oral administration 2 to 3 times a day for the treatment of coronary heart disease or hypertension.

EXAMPLES

Example 1

| Ingredient | Capsule (mg) |
| --- | --- |
| Compound No. 22 (in free base form) | 25.0 |
| Pindolol (in free base form) | 5.0 |
| Lactose | 158.0 |
| Polyvinyl pyrrolidone | 7.5 |
| Magnesium Stearate | 3.0 |
| Silica (colloidal) | 1.5 |
| Total | 200.0 |

Example 2

| Ingredient | Capsule (mg) |
| --- | --- |
| Compound No. 22 | 35.0 |
| Isosorbide dinitrate | 30.0 |
| Pindolol | 7.5 |
| Lactose | 58.0 |
| Mannitol | 150.0 |
| Corn Starch | 15.0 |
| Silica (colloidal) | 1.5 |
| Magnesium stearate | 3.0 |
| Total | 300.0 |

Example 3

| Ingredient | Capsule (mg) |
| --- | --- |
| Compound No. 22 | 35.0 |
| Isosorbide dinitrate | 30.0 |
| Lactose | 65.5 |
| Mannitol | 150.0 |
| Corn Starch | 15.0 |
| Silica (colloidal) | 1.5 |
| Magnesium stearate | 3.0 |
| Total | 300.0 |

Example 4

| Ingredient | Tablet (mg) |
| --- | --- |
| Compound No. 22 (in free base form) | 25.0 |
| Pindolol (in free base form) | 5.0 |
| Polyvinylpyrrolidone | 15.0 |
| Lactose | 185.2 |
| Corn Starch | 30.0 |
| Talcum | 6.0 |

-continued

| Ingredient | Tablet (mg) |
|---|---|
| Silica (colloidal) | 0.8 |
| Magnesium stearate | 3.0 |
| Total | 270.0 |

Example 5

| Ingredient | Tablet (mg) |
|---|---|
| Compound No. 22 | 35.0 |
| Isosorbide dinitrate | 30.0 |
| Pindolol | 7.5 |
| Lactose | 53.5 |
| Mannitol | 150.0 |
| Corn Starch | 15.0 |
| Polyvinylpyrrolidone K 30 | 6.0 |
| Magnesium stearate | 3.0 |
| Total | 300.0 |

Example 6

| Ingredient | Tablet (mg) |
|---|---|
| Compound No. 22 | 35.0 |
| Isosorbide dinitrate | 30.0 |
| Lactose | 61.0 |
| Mannitol | 150.0 |
| Corn Starch | 15.0 |
| Polyvinylpyrrolidone K 30 | 6.0 |
| Magnesium stearate | 3.0 |
| Total | 300.0 |

Example 7

Compound No. 22 in the formulations of Examples 1–6 may be replaced by compound No. 41 to obtain formulations for similar uses.

Example 8

Compound No. 22 in the formulations of Examples 1–6 may be replaced by compound No. 51 to obtain formulations for similar uses.

Example 9

Pindolol in the formulations of Examples 1, 2, 4 and 5 may be replaced by an amount of 1 mg of LT to obtain formulations for similar use.

I claim:

1. A pharmaceutical composition useful in treating coronary heart disease or hypertension comprising a pharmaceutically acceptable carrier or diluent and as the active agents: (1) as component (A), a member selected from the group consisting of 4-(2,1,3-benzoxadiazol-4-yl)-1,4-dihydro-2,6-dimethyl-pyridine-3,5-dicarboxylic acid diethylester, 4-(2,1,3-benzothiadiazole-4-yl)-1,4-dihydro-2,6-dimethyl-pyridine-3,5-dicarboxylic acid dimethylester and 4-(2,1,3-benzoxadiazol-4-yl)-1,4-dihydro-2,6-dimethyl-3-isopropyloxy carbonylpyridine-5-carboxylic acid methyl ester; and (2) as component (B), a β-adrenoceptor blocking agent possessing some degree of intrinsic sympathomimetic activity, the sum of components (A) and (B) in said composition being present in a therapeutically effective amount.

2. A composition of claim 1 containing as component (A), 4-(2,1,3-benzoxadiazol-4-yl)-1,4-dihydro-2,6-dimethyl-pyridine-3,5-dicarboxylic acid diethylester or 4-(2,1,3-benzothiadiazole-4-yl)-1,4-dihydro-2,6-dimethyl-pyridine-3,5-dicarboxylic acid dimethylester.

3. A composition of claim 1 containing as component (B), 4-(2-hydroxy-3-isopropylaminopropoxy)indole (Pindolol) or 4-(2-benzoyloxy-3-tert-butylaminopropoxy)-2-methylindole.

4. A composition of claim 2, containing as a component (A) 4-(2,1,3-Benzoxadiazol-4-yl)-1,4-dihydro-2,6-dimethyl-pyridine-3,5-dicarboxylic acid-diethylester.

5. A composition of claim 1 containing as component (A), 4-(2,1,3-benzoxadiazol-4-yl)-1,4-dihydro-2,6-dimethyl-3-isopropyloxy carbonylpyridine-5-carboxylic acid methyl ester.

6. A composition of claim 2 containing as component (A), 4-(2,1,3-benzothiadiazole-4-yl)-1,4-dihydro-2,6-dimethyl-pyridine-3,5-dicarboxylic acid dimethyl ester.

7. A composition of claim 3, containing as a component (B) Pindolol.

8. A composition of claim 1, wherein the weight ratio of components (A) and (B) is from about 100:1 to about 1:10.

9. A composition of claim 1, consisting of 4(2,1,3-Benzoxadiazol-4-yl)-1,4-dihydro-2,6-dimethyl-pyridine-3,5-dicarboxylic acid diethylester as a component (A) and Pindolol as a component (B).

10. A composition of claim 9, wherein the weight ratio of components (A) and (B) is from about 10:1 to about 1:10.

11. A method of treating coronary heart disease or hypertension which comprises administering to a subject in need of such treatment a composition comprising as the active agents: (1) as component (A), a member selected from the group consisting of 4-(2,1,3-benzoxadiazol-4-yl)-1,4-dihydro-2,6-dimethyl-pyridine-3,5-dicarboxylic acid diethylester, 4-(2,1,3-benzothiadiazole-4-yl)-1,4-dihydro-2,6-dimethyl-pyridine-3,5-dicarboxylic acid dimethylester and 4-(2,1,3-benzoxadiazol-4-yl)-1,4-dihydro-2,6-dimethyl-3-isopropyloxy carbonylpyridine-5-carboxylic acid methyl ester; and (2) as component (B), a β-adrenoceptor blocking agent possessing some degree of intrinsic sympathomimetic activity, the sum of components (A) and (B) in said composition being present in a therapeutically effective amount.

12. A method of claim 11 wherein the component (A) is 4-(2,1,3-benzoxadiazol-4-yl)-1,4-dihydro-2,6-dimethyl-pyridine-3,5-dicarboxylic acid diethylester or 4-(2,1,3-benzothiadiazole-4-yl)-1,4-dihydro-2,6-dimethyl-pyridine-3,5-dicarboxylic acid dimethylester.

13. A method of claim 11 wherein component (B) is 4-(2-hydroxy-3-isopropylaminopropoxy)indole (Pindolol) or 4-(2-benzoyloxy-3-tert-butylaminopropoxy)-2-methylindole.

14. A method of claim 11 wherein component (A) is 4-(2,1,3-benzoxadiazol-4-yl)-1,4-dihydro-2,6-dimethyl-3-isopropyloxy carbonylpyridine-5-carboxylic acid methyl ester.

15. A method of claim 12 wherein component (A) is 4-(2,1,3-benzothiadiazole-4-yl)-1,4-dihydro-2,6-dimethyl-pyridine-3,5-dicarboxylic acid dimethyl ester.

16. A composition of claim 3 containing as component (B), 4-(2-benzoyloxy-3-tert-butylaminopropoxy)-2-methylindole.

17. A method of claim 13 wherein component (B) is 4-(2-hydroxy-3-isopropylaminopropoxy)indole.

18. A method of claim 13 wherein component (B) is 4-(2-benzoyloxy-3-tert-butylaminopropoxy)-2-methylindole.

* * * * *